United States Patent
Prochiantz et al.

(10) Patent No.: US 10,842,852 B2
(45) Date of Patent: Nov. 24, 2020

(54) METHODS OF DELIVERING A POLYPEPTIDE MOLECULE TO OTX2 TARGET CELLS USING AN OTX2 TARGETING PEPTIDE

(71) Applicants: Centre National de la Recherche Scientifique, Paris (FR); Ecole Normale Superieure, Paris (FR)

(72) Inventors: Alain Prochiantz, Paris (FR); Ariel Di Nardo, Palaiseau (FR); Marine Beurdeley, Paris (FR); Takao Hensch, Newton, MA (US)

(73) Assignees: Centre National de la Recherche Scientifique, Paris (FR); Ecole Normale Superieure, Paris (FR)

( * ) Notice: Subject to any disclaimer, the term of this patent is extended or adjusted under 35 U.S.C. 154(b) by 0 days.

(21) Appl. No.: 15/280,502

(22) Filed: Sep. 29, 2016

(65) Prior Publication Data

US 2017/0080060 A1   Mar. 23, 2017

Related U.S. Application Data

(62) Division of application No. 13/145,066, filed as application No. PCT/FR2010/000045 on Jan. 19, 2010, now abandoned.

(30) Foreign Application Priority Data

Jan. 19, 2009 (FR) ..................... 09 00217

(51) Int. Cl.
| | | |
|---|---|---|
| *A61K 38/00* | (2006.01) | |
| *A61K 38/18* | (2006.01) | |
| *A61K 49/00* | (2006.01) | |
| *A61B 5/00* | (2006.01) | |
| *C07K 14/475* | (2006.01) | |
| *C07K 14/48* | (2006.01) | |
| *C07K 14/00* | (2006.01) | |
| *A61K 38/46* | (2006.01) | |
| *C07K 14/47* | (2006.01) | |
| *A61K 47/62* | (2017.01) | |
| *A61K 38/17* | (2006.01) | |
| *C12N 9/16* | (2006.01) | |
| *A61L 27/38* | (2006.01) | |
| *C12N 5/079* | (2010.01) | |
| *C12N 15/85* | (2006.01) | |
| *C12N 5/0793* | (2010.01) | |
| *A61P 27/02* | (2006.01) | |
| *A61P 25/28* | (2006.01) | |
| *C12Q 1/6881* | (2018.01) | |
| *A61P 25/00* | (2006.01) | |

(Continued)

(52) U.S. Cl.
CPC ........ *A61K 38/465* (2013.01); *A61K 38/1709* (2013.01); *A61K 47/62* (2017.08); *C07K 14/47* (2013.01); *C07K 14/4702* (2013.01); *C12N 9/16* (2013.01); *C12Y 301/03001* (2013.01); *A61K 9/0048* (2013.01); *A61K 35/12* (2013.01); *A61K 35/30* (2013.01); *A61L 27/3604* (2013.01); *A61L 27/383* (2013.01); *A61L 2300/252* (2013.01); *A61L 2300/64* (2013.01); *A61P 25/00* (2018.01); *A61P 25/28* (2018.01); *A61P 27/02* (2018.01); *A61P 43/00* (2018.01); *C07K 2319/00* (2013.01); *C07K 2319/03* (2013.01); *C07K 2319/33* (2013.01); *C12N 5/0602* (2013.01); *C12N 5/0618* (2013.01); *C12N 5/0619* (2013.01); *C12N 5/0621* (2013.01); *C12N 5/16* (2013.01); *C12N 15/85* (2013.01); *C12N 15/907* (2013.01); *C12N 2501/40* (2013.01); *C12N 2501/50* (2013.01); *C12N 2501/58* (2013.01); *C12N 2502/085* (2013.01); *C12N 2506/08* (2013.01); *C12N 2830/008* (2013.01); *C12Q 1/6881* (2013.01); *G01N 33/5005* (2013.01); *G01N 33/5044* (2013.01); *G01N 33/5058* (2013.01); *G01N 33/57496* (2013.01); *G01N 2500/10* (2013.01); *G01N 2800/164* (2013.01); *G01N 2800/168* (2013.01)

(58) Field of Classification Search
CPC .............. A61K 38/00; A61K 47/48238; A61K 47/48284; C07K 19/00; C07K 2319/00; C07K 2319/35; C12N 2710/24132
See application file for complete search history.

(56) References Cited

U.S. PATENT DOCUMENTS

| 7,858,346 B2 | 12/2010 | Furukawa |
| 2002/0132753 A1 | 9/2002 | Rosen et al. |

(Continued)

FOREIGN PATENT DOCUMENTS

| CN | 1342679 | * | 4/2002 |
| FR | 2926023 A1 | | 7/2009 |

(Continued)

OTHER PUBLICATIONS

Bourin et al., Fundamental. & Clinical Pharmacology, 2007:21:567-574.*

(Continued)

*Primary Examiner* — Chang-Yu Wang
(74) *Attorney, Agent, or Firm* — Morgan, Lewis & Bockius LLP

(57) ABSTRACT

The disclosure provides a method of delivering a polypeptide molecule to an Otx2 target cell, including contacting the target cell with a chimeric polypeptide having (i) a targeting peptide consisting of SEQ ID NO: 2 and (ii) the polypeptide molecule.

5 Claims, 7 Drawing Sheets

Specification includes a Sequence Listing.

(51) Int. Cl.

| | | |
|---|---|---|
| A61L 27/36 | (2006.01) | |
| A61P 43/00 | (2006.01) | |
| C12N 15/90 | (2006.01) | |
| C12N 5/16 | (2006.01) | |
| C12N 5/071 | (2010.01) | |
| G01N 33/50 | (2006.01) | |
| A61K 35/30 | (2015.01) | |
| G01N 33/574 | (2006.01) | |
| A61K 9/00 | (2006.01) | |
| A61K 35/12 | (2015.01) | |

(56) References Cited

U.S. PATENT DOCUMENTS

| | | |
|---|---|---|
| 2002/0142299 A1 | 10/2002 | Davidson et al. |
| 2003/0186890 A1 | 10/2003 | Drin et al. |
| 2007/0192889 A1 | 8/2007 | La Rosa et al. |
| 2008/0229439 A1 | 9/2008 | La Rosa et al. |
| 2008/0233648 A1 | 9/2008 | Sugaya et al. |
| 2011/0065646 A1 | 3/2011 | Prochiantz et al. |

FOREIGN PATENT DOCUMENTS

| | | | |
|---|---|---|---|
| WO | 96/16989 A1 | | 6/1996 |
| WO | 00/29427 A2 | | 11/1999 |
| WO | 02/101232 A2 | | 12/2002 |
| WO | WO02/101232 | * | 12/2002 |
| WO | 2004/069268 A1 | | 8/2004 |
| WO | 2006/046492 A1 | | 5/2006 |
| WO | 2009/106767 A2 | | 9/2009 |

OTHER PUBLICATIONS

Fisch et al. Transgenic and Knockout Models of Neuropsychiatric Disorders, p. 3-69, published 2006, Humana Press.*
Ramos et al. Trends in Pharmacol. Sci. available online Aug. 28, 2006; 29: 493-498.*
Mao et al. English-translated version of CN1342679, published Apr. 3, 2002.*
Tinland et al. PNAS, 1992; 89:7442-7446.*
Holland et al., BMC Biol. 2007; 5:47; doi:10.1186/1741-7007-5-47.*
Heinnbucher et al., Mol. Cell. Biol. 2007; 27:340-351.*
The factsheet of amino acids, pepides and proteins retrieved from the Biology Libre Text website: bio.libretexts.org/Bookshelves/Microbiology/Book%3A_Microbiology_(Kaiser)/Unit_7%3A_Microbial_Genetics_and_Microbial_Metabolism/19%3A_Review_of_Molecular_Genetics/19.1%3A_Polypeptides_and_Proteins on Nov. 26, 2019.*
Simeone et al. Curr. Opin. Genet. Dev. 2002; 12:409-415.*
Stewart et al., Nat. Struct. Biol. 1999; 6:301-302.*
Fei et al., Invest. Ophthalmol. Vis. Sci. 2000; 41:2849-2856.*
Topisirovic et al. Histol. Histopathol., 2005; 20:1275-1284.*
Sugiyama et al. Cell, 2008; 134: 508-520.*
Joliot et al., PNAS, 1991; 88:1864-1868.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Derossi et al., "Trojan peptides: the penetratin system for intracellular delivery," Trends in Cell Biology, 8: 84-87 (1998).
Prochiantz, "Messenger proteins: homeoproteins, TAT and others," Current Opinion in Cell Biology, 12: 400-406 (2000).
Fonseca et al., "Recent advances in the use of cell-penetrating peptides for medical and biological applications," Advanced Drug Delivery Reviews, 61: 953-964 (2009) (abstract only).
Prochiantz, "Protein and peptide transduction, twenty years later a happy birthday," Advanced Drug Delivery Reviews, 60: 448-451 (2008).
Joliot et al., "Transduction peptides: from technology to physiology," Nature Cell Biology, 6: 189-196 (2004).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology, 111: 2129-2138 (1990).
Bowie et al., "Deciphering the Message in Protein Sequences: Tolerance to Amino Acid Substitutions," Science, 247: 1306-1310 (1990).
Pawson et al., "Assembly of Cell Regulatory Systems Through Protein Interaction Domains," Science, 300: 445-452 (2003).
Baas et al., "The subcellular localization of OTX2 is cell-type specific and developmentally regulated in the mouse retina," Molecular Brain Research, 78: 26-37 (2000).
Huang et al., "Time to Change: Retina Sends a Messenger to Promote Plasticity in Visual Cortex," Neuron, 59: 355 (2008).
Rath et al., "Ontogenetic expression of the Otx2 and Crx homeobox genes in the retina of the rat," Experimental Eye Research, 85: 65-73 (2007).
Rebsam et al., "Otx2's Incredible Journey," Cell, 134: 386-387 (2008).
Sugiyama et al., "From brain formation to plasticity: Insights on Otx2 homeoprotein," Development, Growth & Differentiation, 51: 369-377 (2009).
Sugiyama et al., "Experience-Dependent Transfer of Otx2 Homeoprotein into the Visual Cortex Activates Postnatal Plasticity," Cell, 134: 508-520 (2008).
Prochiantz, "Processus Morphologiques," College de France, 260-262 (2007).
Database UniProt, Database Accession No. P32243 (1993).

* cited by examiner

Figure 1

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Targeting peptide
<220> FEATURE:
<221> NAME/KEY: VARIANT
<222> LOCATION: (1)..(2)
<223> OTHER INFORMATION: Arg or Lys
<220> FEATURE:
<221> NAME/KEY: VARIANT
<222> LOCATION: (3)..(3)
<223> OTHER INFORMATION: Asn or Gln
<220> FEATURE:
<221> NAME/KEY: VARIANT
<222> LOCATION: (4)..(5)
<223> OTHER INFORMATION: Arg or Lys
```

```
<220> FEATURE:
<221> NAME/KEY: VARIANT
<222> LOCATION: (6)..(6)
<223> OTHER INFORMATION: Asp or Glu
<220> FEATURE:
<221> NAME/KEY: VARIANT
<222> LOCATION: (7)..(7)
<223> OTHER INFORMATION: Arg or Lys
<220> FEATURE:
<221> NAME/KEY: VARIANT
<222> LOCATION: (8)..(9)
<223> OTHER INFORMATION: Thr or Ser
<220> FEATURE:
<221> NAME/KEY: VARIANT
<222> LOCATION: (10)..(10)
<223> OTHER INFORMATION: Phe or Tyr or Trp
<220> FEATURE:
<221> NAME/KEY: VARIANT
<222> LOCATION: (11)..(11)
<223> OTHER INFORMATION: Thr or Ser
<220> FEATURE:
<221> NAME/KEY: VARIANT
<222> LOCATION: (12)..(12)
<223> OTHER INFORMATION: Arg or Lys
<220> FEATURE:
<221> NAME/KEY: VARIANT
<222> LOCATION: (13)..(13)
<223> OTHER INFORMATION: Ala or Gly
<220> FEATURE:
<221> NAME/KEY: VARIANT
<222> LOCATION: (14)..(14)
<223> OTHER INFORMATION: Asn or Gln
<220> FEATURE:
<221> NAME/KEY: VARIANT
<222> LOCATION: (15)..(15)
<223> OTHER INFORMATION: Leu or Ile or Val

<400> SEQUENCE: 1

Xaa Xaa Xaa Xaa Xaa Xaa Xaa Xaa Xaa Xaa Xaa Xaa Xaa Xaa Xaa
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Targeting peptide

<400> SEQUENCE: 2

Arg Lys Gln Arg Arg Glu Arg Thr Thr Phe Thr Arg Ala Gln Leu
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Targeting peptide: inactive mutant

<400> SEQUENCE: 3

Ala Ala Gln Arg Arg Glu Arg Thr Thr Phe Thr Arg Ala Gln Leu
1               5                   10                  15

<210> SEQ ID NO 4
<211> LENGTH: 45
<212> TYPE: PRT
<213> ORGANISM: Artificial Sequence
<220> FEATURE:
<223> OTHER INFORMATION: VP16 transactivator domain

<400> SEQUENCE: 4

Met Leu Gly Asp Gly Asp Ser Pro Gly Pro Gly Phe Thr Pro His Asp
```

-continued

```
1               5                   10                  15
Ser Ala Pro Tyr Gly Ala Leu Asp Met Ala Asp Phe Glu Phe Glu Gln
            20                  25                  30

Met Phe Thr Asp Ala Leu Gly Ile Asp Glu Tyr Gly Gly
        35                  40                  45
```

METHODS OF DELIVERING A POLYPEPTIDE MOLECULE TO OTX2 TARGET CELLS USING AN OTX2 TARGETING PEPTIDE

This invention was made with government support under grant number OD003699 awarded by the National Institutes of Health. The Government has certain rights in the invention.

SEQUENCE LISTING SUBMISSION VIA EFS-WEB

A computer readable text file, entitled "045636-5170_SequenceListing.txt," created on or about Aug. 29, 2011, with a file size of about 3 kb contains the sequence listing for this application and is hereby incorporated by reference in its entirety.

The present invention relates to polypeptides which enable the specific targeting of a molecule of interest to homeoprotein Otx2 target cells, and in particular to retinal ganglion neurons and retinal bipolar neurons.

The retina is the cell sheet coating the back of the eye. It contains various types of neurons, the role of which is to be capture light energy and to convert it into a nerve signal, and also glial cells.

Schematically, the retina comprises three main layers of neurons: photoreceptor neurons (cones and rods), bipolar neurons and ganglion neurons; other neurons, the anarine neurons and the horizontal neurons, play a regulatory role. The photoreceptor neurons react to light, and the signal that they generate is transmitted, by means of the bipolar neurons, to the ganglion neurons, the axons of which constitute the nerve fibers of the optic nerve, sending information to the brain.

The degeneration of retinal neurons is implicated in various retinopathies. Thus, the degeneration of photoreceptor neurons is implicated in certain pathological conditions, such as pigmentary retinitis or macular degeneration. In other pathological conditions, such as glaucoma, it is mainly the ganglion neurons which are affected.

Otx2 (Orthodenticle homolog 2) is a homeoprotein containing a bicoid-type homeodomain (Simeone et al., Embo J, 12, 2735-47, 1993). It belongs to the Otx homeoprotein family, which plays a fundamental role in brain development during embryogenesis (Acampora et al., Prog Neurobiol, 64, 69-95, 2001; Simeone et al., Curr Opin Genet Dev, 12, 409-15, 2002).

During previous studies, the team of the inventors demonstrated the positive effect of a homeoprotein, Otx2 (Orthodenticle homolog 2), on the survival of retinal ganglion neurons. These results are reported in PCT application WO/2009/106767.

Otx2 (Orthodenticle homolog 2) is a homeoprotein containing a bicoid-type homeodomain (Simeone et al., Embo J, 12, 2735-47, 1993). It belongs to the Otx homeoprotein family, which plays a fundamental role in brain development during embryogenesis (Acampora et al., Prog Neurobiol, 64, 69-95, 2001; Simeone et al., Curr Opin Genet Dev, 12, 409-15, 2002). It has also been shown that Otx2 plays a role in post-natal development of the cerebral cortex, and in particular in its plasticity. Otx, which is synthesized in the retina, is transported to the visual cortex, where it is taken up by the parvalbumin neurons of the visual cortex, thereby inducing their maturation, and leads first to the opening, and then, some time later, the closing of the critical period of plasticity (Sugiyama et al., Cell, 134, 508-20, 2008).

A critical period of plasticity is a phase of post-natal development represented by a time interval of limited duration (variable according to animal species and according to the sensory function involved) during which the sensory stimuli are capable of modifying the functional organization of the corresponding cortical zones.

In continuing their research, the inventors have discovered that, in the retina, Otx2 binds specifically to ganglion neurons and to bipolar neurons, and have identified the region of Otx2 that is responsible for this binding. They have also shown that this same region is also responsible for the targeting of Otx2 to the parvalbumin neurons of the visual cortex, by interacting with the perineuronal net of chondroitin sulfate proteoglycans which surrounds these neurons, and that it makes it possible, by competing with the endogenous Otx2 protein taken up by the parvalbumin neurons, to inhibit this uptake. This inhibition leads to the return of these neurons to an immature state, enabling re-opening of the critical phase of plasticity.

The region responsible for the targeting of Otx2 to its target cells is made up of a peptide sequence of 15 amino acids. The inventors have also noted that this polypeptide, isolated, has the same binding specificity as the whole Otx2 protein.

A subject of the present invention is an isolated cell targeting polypeptide defined by the sequence $B_1B_2X_1B_3B_4X_2B_5X_3X_4X_5X_6B_6X_7X_8X_9$ (SEQ ID NO: 1), in which:

$B_1$, $B_2$, $B_3$, $B_4$, $B_5$ et $B_6$ represent independently arginine or lysine;

$X_1$ and $X_8$ are independently asparagine or glutamine;

$X_2$ represents aspartic acid or glutamic acid;

$X_3$, $X_4$ and $X_6$ represent independently threonine or serine;

$X_5$ represents phenylalanine, tyrosine or tryptophan;

$X_7$ represent alanine or glycine;

$X_9$ represents leucine, isoleucine or valine.

This polypeptide, in the presence of retinal cells, binds specifically to ganglion neurons and to bipolar neurons.

Preferred embodiments of the present invention are polypeptides in which:

at least one of the amino acids $B_1$, $B_3$, $B_4$, $B_5$ and $B_6$ is an arginine; and/or $B_2$ is a lysine; and/or at least one of the amino acids $X_1$ and $X_8$ is a glutamine; and/or $X_2$ is a glutamic acid; and/or at least one of the amino acids $X_3$, $X_4$ and $X_6$ is a threonine; and/or $X_5$ is a phenylalanine; and/or $X_7$ is an alanine; and/or $X_9$ is a leucine.

According to one particularly preferred embodiment of a cell targeting polypeptide in accordance with the invention, it is defined by the following sequence: RKQRRERTTF-TRAQL (SEQ ID NO: 2).

The amino acids constituting a polypeptide in accordance with the invention may be natural amino acids of the L series. It is also possible to replace all or some of these amino acids with their isomers of the D series, in order to increase the stability of the polypeptide in vivo. The amino acids, of the L series or of the D series, may also, where appropriate, be linked according to a reverse sequence of the sequence SEQ ID NO: 1 or of the sequence SEQ ID NO: 2, which sequences are indicated above.

A subject of the present invention is also the use of a cell targeting polypeptide in accordance with the invention, for enabling the specific targeting of a cargo of interest to Otx2 target cells.

By way of examples of Otx2 target cells, mention will be made, in addition to the retinal ganglion neurons and retinal bipolar neurons already mentioned above, of the neurons coated in a perineuronal net of chondroitin sulfate proteoglycans, which includes in particular neurons expressing parvalbumin (PV neurons) located in particular in the visual cortex. Other Otx2 target cells are neurons of the midbrain, in particular the dopaminergic neurons of the substantia nigra and of the ventral tegmental area, and their synaptic targets.

Other Otx2 target cells can be easily identified by means of a targeting polypeptide in accordance with the invention, for example by combining said polypeptide with a label, by bringing said labeled polypeptide into contact with a sample of a tissue or of an organ to be tested, and by detecting, in said sample, the presence or absence of cells binding said polypeptide, and in the case of the presence of cells binding said polypeptide, their localization.

The general term "cargo" denotes any molecule or molecular complex that it is desired to target to a target cell.

The cargos that can be transported by cell targeting polypeptides in accordance with the invention may be of very varied nature: they may be chemical molecules, macromolecules, for instance proteins or nucleic acids, or particles such as liposomes, nanoparticles, or viral or virus-like particles. They may be labels intended to make it possible to detect and/or localize Otx2 target cells in a tissue or an organ, or active ingredients that it is desired to specifically target to Otx2 target cells.

If it is desired to obtain not only the targeting of the cargo of interest to the target cell, but also its entry into said cell, a cell targeting polypeptide in accordance with the invention can advantageously be associated with a transducer polypeptide.

Transducer polypeptides are polypeptides comprising a sequence called a "transduction domain" which confers on them the ability to penetrate inside a living cell, independently of the presence of specific transporters or receptors.

A very large number of transducer polypeptides are known per se. By way of nonlimiting examples, mention will be made of: penetratins, which are polypeptides derived from the third helix of a homeodomain; polypeptides derived from the Tat protein of HIV1, and in particular from fragment 48-60 of said protein; polyarginines; polypeptides derived from the VP22 protein of HSV; polypeptides derived from a signal sequence conjugated to a nuclear localization sequence; transportans which are derived from a fusion between a portion of a neuropeptide, galanin, and a wasp venom polypeptide.

The subject of the present invention is also an isolated polypeptide containing a cell targeting polypeptide in accordance with the invention and a transducer polypeptide.

This polypeptide may be an isolated fragment of Otx2 comprising the entire homeodomain, and the 2 amino acids immediately preceding said homeodomain. This fragment may also be deleted of a part of the sequence of the homeodomain, provided that the targeting sequence in accordance with the invention and at least the third helix of the homeodomain are retained.

The polypeptide may also be a chimeric polypeptide associating a cell targeting polypeptide in accordance with the invention with a heterologous transducer polypeptide. In this context, preferred transducer polypeptides are those of the penetratin family. It is thus possible to associate a cell targeting polypeptide in accordance with the invention with a homeodomain fragment of a homeoprotein other than Otx2, comprising at least the third helix of said homeodomain, or else with penetratin derivatives such as those described, for example, in PCT applications WO 00/01417 or WO 00/29427.

A subject of the present invention is also compositions comprising a cell targeting polypeptide in accordance with the invention, optionally associated with a transducer polypeptide, bonded to a cargo.

The bonding between the cell targeting polypeptide in accordance with the invention and the cargo can be carried out in various ways, known per se, according in particular to the nature of the cargo concerned, and the envisaged modes of use. Generally, the cell targeting polypeptide (optionally fused with a transducer polypeptide) and the cargo will be covalently associated, where appropriate by means of a spacer arm, for example a peptide linker. They may also be noncovalently associated, by means of ionic or hydrophobic interactions; in this case, the targeting polypeptide may be bonded to a molecule capable of noncovalently bonding to the cargo. This molecule may in particular be a transducer polypeptide such as a penetratin, capable of bonding, via hydrophobic interactions, to a cargo having one or more hydrophobic domains, as described in PCT application WO 04/069279.

According to one particular embodiment of a composition in accordance with the invention, said composition is in the form of a chimeric polypeptide, comprising a cell targeting polypeptide in accordance with the invention, bonded with one or more polypeptide sequences constituting the cargo, and optionally with a transducer polypeptide. The order in which the cell targeting polypeptide, the transducer polypeptide and the polypeptide sequences constituting the cargo are arranged is not essential.

By way of nonlimiting examples of chimeric polypeptides in accordance with the invention, mention will be made of chimeric polypeptides comprising a cell targeting polypeptide in accordance with the invention, a transducer polypeptide, one or more transcription-regulating sequences and/or one or more translation-regulating sequences. The term "chimeric polypeptide" is used herein in its usual sense, to denote polypeptides associating sequences of different origins, which therefore excludes natural Otx2 proteins.

Many transcription-regulating or translation-regulating sequences are known per se.

By way of examples, mention will be made of:
transcription-activating sequences, such as, for example, the VP16 trans-activator of the HSV virus (herpes simplex virus);
transcription-repressing sequences, such as that of Engrailed (corresponding, for example, to amino acids 1-298 of the Engrailed protein of *Drosophila melanogaster* (GenBank AAA65478));
translation-regulating (in particular activating) sequences, such as eIF4E-binding sites which are, for example, detected in many homeoproteins (for a review, cf. Topisirovic & Borden, Histol. Histopathol., 20, 1275-1284, 2005), including Otx2.

The chimeric polypeptides in accordance with the invention can be obtained by various methods that are well-known per se, in particular by peptide synthesis, or by conventional generic engineering techniques.

Chimeric polypeptides in accordance with the invention comprising a cell targeting polypeptide, a transducer polypeptide, one or more transcription-regulating sequences and/or one or more translation-regulating sequences can be used in the same applications as the natural Otx2 protein, and in particular for increasing the survival of Otx2 target cells. They can thus be used in particular for preventing or treating the degeneration of retinal ganglion neurons and/or retinal bipolar neurons, which are involved in particular in glaucoma, and also in various optical, genetic or vascular neuropathies, for example pigmentary retinitis or optic nerve damage. They can also be used in the context of the treatment of certain neurodegenerative diseases (such as, for example, Alzheimer's disease, multiple sclerosis or Parkinson's disease). Generally, these chimeric polypeptides may be used in said applications according to the same modes as those described for Otx2 in PCT application WO 2009/106767.

In order to implement the present invention, all that is needed is to bring said chimeric polypeptide into contact with the target cells; it in fact penetrates inside said cells by means of the internalization sequence provided by the transducer polypeptide. Preferably, said bringing into contact is carried out at a concentration of said chimeric polypeptide of from 0.5 to 10 nM, advantageously from 1 to 5 nM, and particularly advantageously from 1.5 to 3 nM.

In vitro, all that is needed is to add said chimeric polypeptide to the neuron culture medium. In vivo, it can be administered via various routes, locally, in particular by injection or infusion into the vitreous humor or into the infraorbital space, or in the form of an eyewash or of an ophthalmic ointment. It can also be administered using a controlled-release device, for example in the form of an intraocular implant. Where appropriate, it can be administered systemically, for example by intravenous injection.

The doses of chimeric polypeptide to be administered in vivo in order to obtain the desired concentration in contact with the target cells can be readily be determined and adjusted by those skilled in the art depending, in particular, on the methods of administration envisaged.

This contact can also be brought about by placing the target cells in the presence of cells that have been transformed so as to express or overexpress, and secrete, said chimeric polypeptide. In vitro, this can be carried out by coculturing these transformed cells with the cells. In vivo, cells transformed so as to express or overexpress, and secrete, said chimeric polypeptide can, for example, be grafted into the retina.

It is also possible, where appropriate, to combine said chimeric polypeptide with one or more other therapeutic active ingredients, in a joint or separate administration.

Cell targeting polypeptides in accordance with the invention can also be used for inhibiting the binding of Otx2 to its target cells, and in particular to parvalbumin neurons coated in a perineuronal net of chondroitin sulfate proteoglycans, so as to make it possible to restore their plasticity. They can thus be used for the treatment of diseases resulting from a defective development, during the critical period of plasticity, of a region of the brain containing the target cells concerned. By way of example, they can be used in the context of the treatment of amblyopia, or in the context of the treatment of neurological or psychiatric diseases such as anxiety disorders, post-traumatic stress syndrome, and also manic-depressive psychosis or schizophrenia. They can also be used in the context of restoring physiological and morphological plasticity in pathological conditions or strokes which lead to the loss of neurons.

In order to inhibit the binding of Otx2 to its target cells, the cell targeting polypeptide in accordance with the invention will be used in such a way as to obtain, on contact with said target cells, a concentration of said polypeptide which is at least 10 times greater, preferably 100 to 1000 times greater, than the concentration of Otx2. Typically, said polypeptide may be used at a concentration of from 1 to 10 µM, advantageously from 10 to 100 µM, and particularly advantageously from 100 to 1000 µM.

For the use in vivo in order to inhibit the binding of Otx2 to its target cells, said targeting polypeptide will preferably be administered locally, for example by means of an osmotic minipump implanted in the brain.

The doses of chimeric polypeptide to be administered in vivo in order to obtain the desired concentration on contact with the target cells can be readily determined and adjusted by those skilled in the art depending, in particular, on the administration methods envisaged.

Cell targeting polypeptides in accordance with the invention can also be used to screen for other molecules capable of binding specifically to Otx2 target cells.

In this context, a subject of the present invention is a method of screening for molecules capable of binding specifically to Otx2 target cells, at the same binding sites as Otx2, characterized in that it comprises:
  bringing a cell targeting polypeptide in accordance with the invention into contact with Otx2 target cells and cells which do not bind Otx2, and with each test molecule;
  selecting the molecules which are capable of inhibiting the binding of said cell targeting polypeptide to the Otx2 target cells, and which do not bind to the cells which do not bind Otx2.

Advantageously, said method is carried out in the presence both of Otx2 target cells and of cells which do not bind Otx2, for example on a section of retina.

The present invention will be understood more clearly by means of the further description which follows, which refers to nonlimiting examples illustrating the identification of a targeting polypeptide in accordance with the invention and the demonstration of its targeting specificity.

BRIEF DESCRIPTION OF DRAWINGS

FIG. 1 depicts, diagrammatically, various constructions carried out. signal seq.: signal peptide of alkaline phosphatase; Alkaline Phosphatase: alkaline phosphatase, Nt: N-terminal region of Otx2 (amino acids 1-37); Hd: homeodomain of Otx2 (amino acids 38-97); Ct: C-terminal region of Otx2 (amino acids 98-289); 6xHis: polyhistidine tag.

µm; (E) AP-Nt-Otx2; (F) AP-HdAA-Otx2; (G) AP-Nt-Otx2 in the presence of RK-Otx2; (H) AP-Nt-Otx2 in the presence of AA-Otx2.

Figure 7:
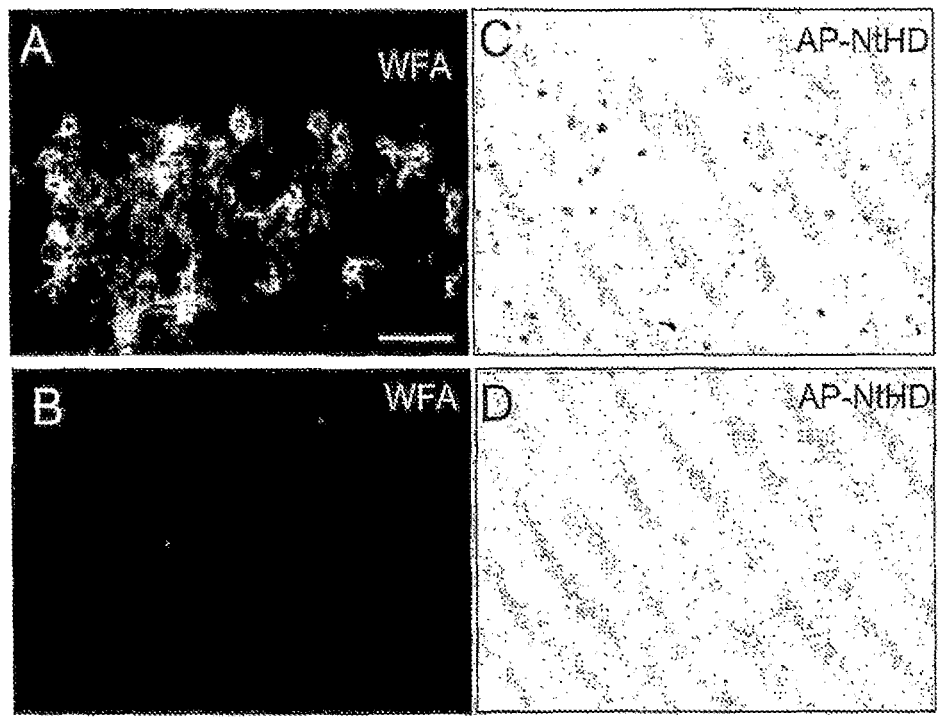

FIG. 7 depicts results from experiments to determine whether the perineuronal net associated with parvalbumin neurons was involved in the binding between AP-Nt-Otx2 and its target cells. (A) and (B) labeling with WFA; (C) and (D) incubation in the presence of AP-Otx2; (A) and (C) untreated sections; (B) and (D) sections treated with chondroitinase ABC.

Figure 8:
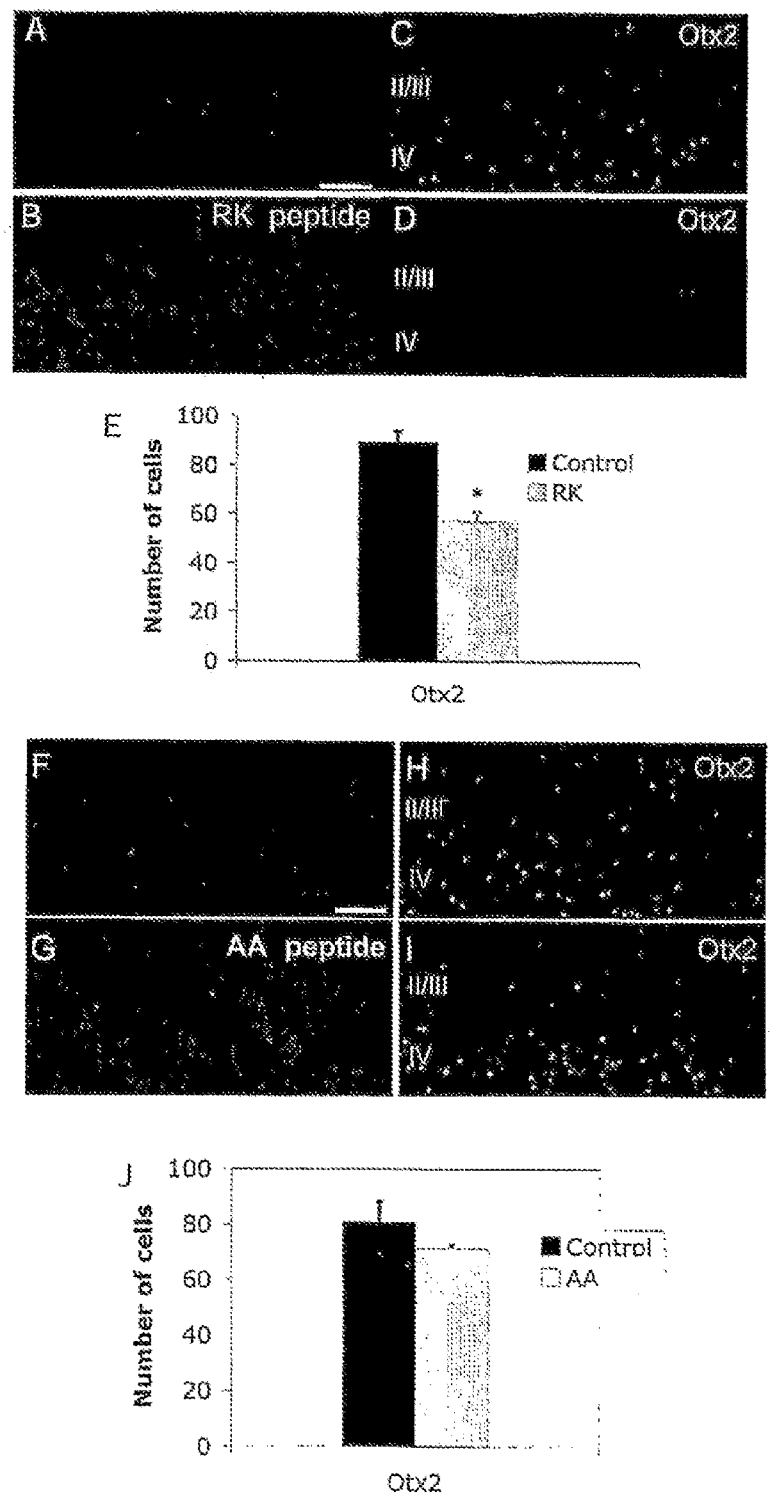

FIG. 8 depicts results obtained with RK-Otx2 peptide. A-E: Infusion of RK-Otx2 (scale bar=100 µm); A, B: Detection of the RK-Otx2 peptide; A: control hemisphere; B: infused hemisphere; C, D: Detection of Otx2; C: control hemisphere; D: infused hemisphere; E: Quantification of the cells expressing Otx2; black bars: control hemisphere; gray bars: infused hemisphere; F-J: Infusion of AA-Otx2 (scale bar=100 µm); F, G: Detection of the AA-Otx2 peptide; A: control hemisphere; B: infused hemisphere; H, I: Detection of Otx2; H: control hemisphere; I: infused hemisphere; J: Quantification of the cells expressing Otx2; black bars: control hemisphere; gray bars: infused hemisphere; *p<0.005, paired Student's t-test; the error bars represent the standard error of the mean.

Figure 9:
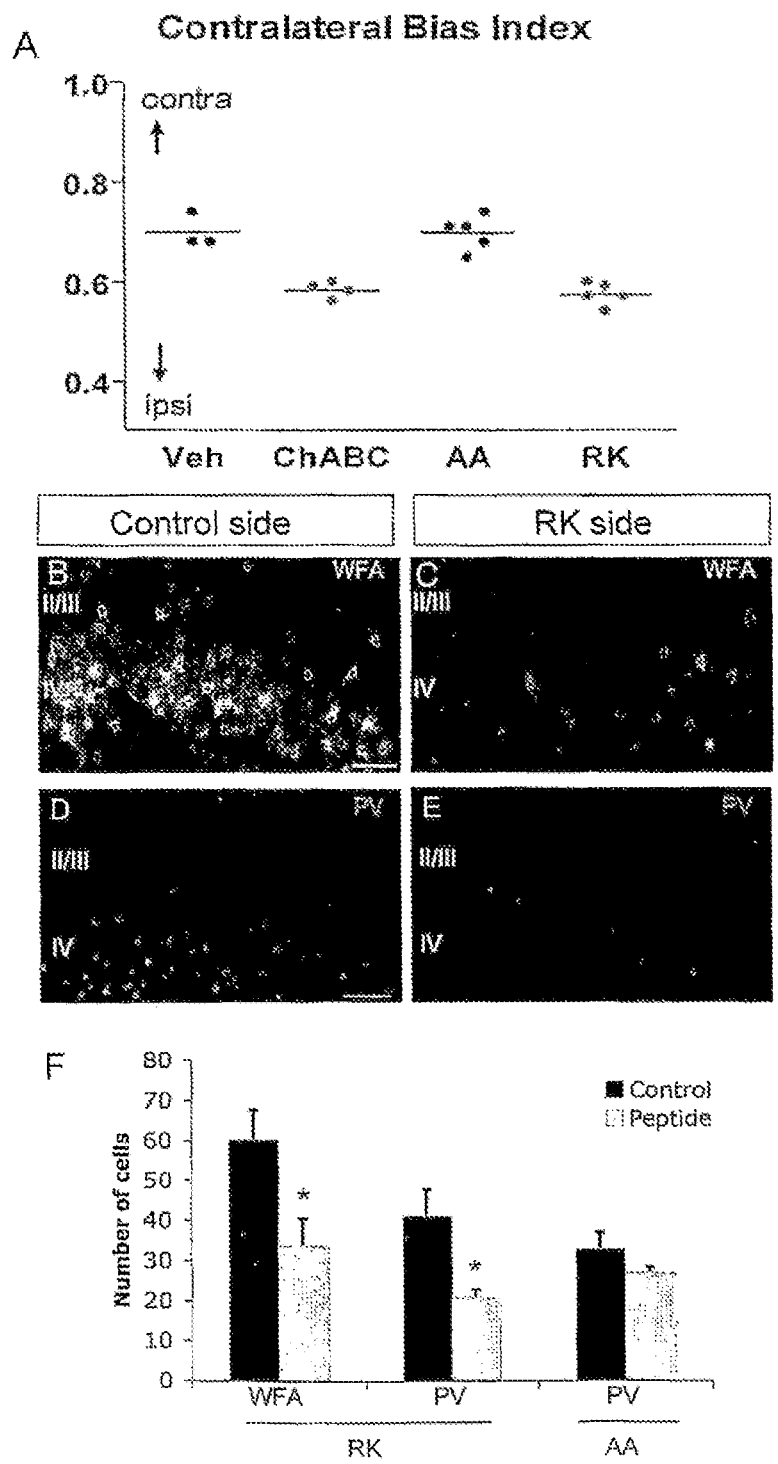

FIG. 9 depicts results obtained from the experiments of Example 5. A: Contralateral bias index after infusion of the RK-Otx2 peptide (RK) or of the AA-Otx2 peptide (AA), or after injection of chondroitinase ABC (chABC) or of injection buffer alone (Veh); B-E: Labeling with WFA (B and C) and expression of parvalbumin (D and E) in the supragranular region of the visual cortex of the hemisphere infused with the RK peptide (C and E), and of the noninfused hemisphere (scale bar=100 µm); F: Quantification of the cells labeled with WFA and of the cells expressing parvalbumin after infusion of the RK-Otx2 peptide (RK) or of the AA-Otx2 peptide (AA); black bars: control hemisphere; gray bars: infused hemisphere; *p<0.05, paired Student's t-test; the error bars represent the standard error of the mean.

EXAMPLE 1: IDENTIFICATION OF A SEQUENCE WHICH TARGETS OTX2 TO RETINAL GANGLION AND RETINAL BIPOLAR NEURONS

During previous experiments (cf. application PCT/FR 2009/000031 of Jan. 9, 2009), it was noted that Otx2 injected into the eye was concentrated essentially in the retinal ganglion neurons (RGCs).

In order to investigate whether a cell targeting domain was present in the sequence of Otx2, chimeric proteins comprising an alkaline phosphatase domain coupled to the whole Otx2 protein or to various fragments of this protein were constructed.

The following fusion proteins were constructed:
Alkaline Phosphatase-whole Otx2 (AP-Otx2)
Alkaline Phosphatase-C-terminal region+homeodomain of Otx2 (AP-Ct-Otx2)
Alkaline Phosphatase-N-terminal region+homeodomain of Otx2 (AP-Nt-Otx2)
Alkaline Phosphatase-homeodomain of Otx2 (AP-Hd-Otx2).

Figure 1:
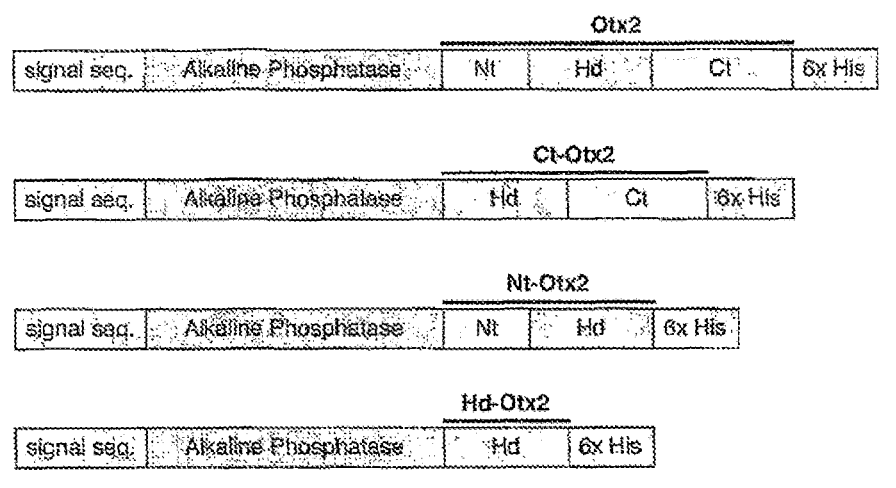

The sequences encoding the human Otx2 protein or encoding the fragments tested were cloned into the vector pAPtag-5 (GenHunter), in frame with the sequence encoding alkaline phosphatase. The various constructions carried out are represented diagrammatically in FIG. 1. HEK 293 cells cultured in culture dishes 10 cm in diameter were transfected with 10 µg of each of the vectors constructed, purified beforehand, using Lipofectamine 2000 (Invitrogen) according to the manufacturer's instructions. The transfected cells were incubated for 48 hours in DMEM/F12, supplemented with 10% of fetal bovine serum (FCS). The supernatant was collected, centrifuged at 100×g for 5 minutes and stored at −80° C. This supernatant is used, without purification, for testing the binding of the chimeric proteins on sections of retina.

To carry out the binding test, cryostat sections (20 µm) of frozen fresh retinas are fixed for 8 minutes in 100% cooled methanol, and then washed 3 times 10 in phosphate buffer (PBS) with 4 mM of $MgCl_2$.

The sections are incubated in PBS buffer, 4 mM $MgCl_2$, plus 10% FCS for 1 hour at room temperature (RT).

For the binding, the supernatants containing the fusion proteins tested are diluted to 1/20 in PBS and incubated for 2 hours at room temperature.

The sections are then washed 5 times in PBS, 4 mM $MgCl_2$, and the bound ligands are then fixed for 2 minutes (60% acetone, 4% PFA, 20 mM Hepes, pH 7).

After 3 washes in PBS, the sections are heated at 65° C. for 2 hours in PBS in order to inactivate the endogenous phosphatases. The sections are then washed twice in PBS before visualization of the alkaline phosphatase activity (preincubation of the sections for 5 minutes in 100 mM Tris, pH 9.5, 100 mM NaCl, 5 mM $MgCl_2$, followed by the addition of NBT/BCIP (Promega)).

Figure 2:
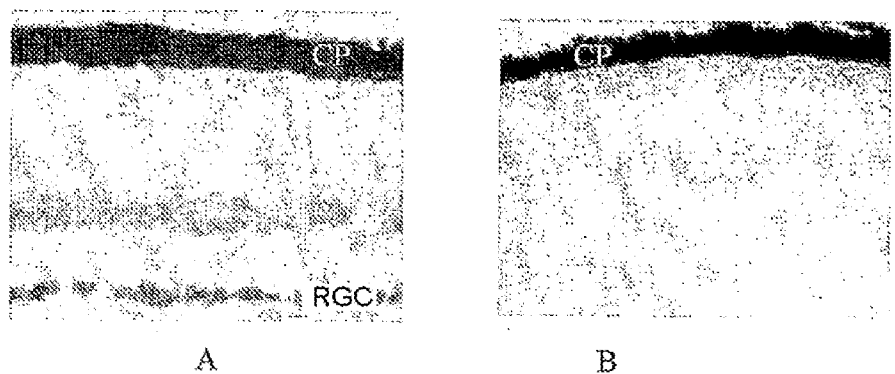
FIG. 2 depicts results obtained with the AP-Nt-Otx2 and AP-Hd-Otx2 fusion proteins. A: Labeling obtained with the AP-Nt-Otx2 fusion protein; B: Labeling obtained with the AP-Hd-Otx2 fusion protein; CP: Cells of the retinal pigment epithelium; Cb: bipolar cells; RGC: ganglion cells.

The results obtained with the AP-Nt-Otx2 and AP-Hd-Otx2 fusion proteins are illustrated by FIG. 2.

These results show that the fusion protein comprising the N-terminal domain of Otx2 and its homeodomain binds specifically to the RGCs and the bipolar cells, whereas the fusion protein containing only the homeodomain does not bind to any of the retinal cells.

Biotinylated peptides corresponding to various fragments of the N-terminal domain+homeodomain portion of Otx2 were synthesized and the binding thereof to sections of retina, prepared as described above, was tested. The incubation of the peptides with the sections of retina was carried out under the same conditions as those described above, and then the sections bearing the bound peptides were incubated with alkaline phosphatase-labeled streptavidin, and the alkaline phosphatase activity was detected as described above.

One of the peptides tested (RK-Otx2), corresponding to the sequence RKQRRERTTFTRAQL (SEQ ID NO: 2), has the same binding specificity as the AP-Otx2 and AP-Nt-Otx2 fusion proteins.

Mutations were then created in this polypeptide. One of the mutants (AA-Otx2), in which two basic amino acids (RK) are exchanged for two neutral amino acids (AA) and which therefore corresponds to the sequence AAQRRERTTFTRAQL (SEQ ID NO: 3), does not inhibit any binding to the retinal cells.

Figure 3:
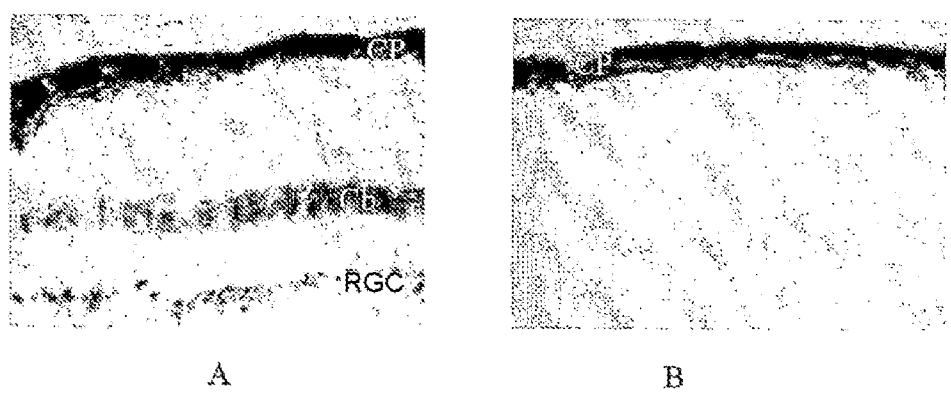
FIG. 3 depicts results obtained with mutant AA-Otx2. A: Labeling obtained with the RK-Otx2 peptide; B: Labeling obtained with the AA-Otx2 peptide; CP: Cells of the retinal pigment epithelium; Cb: bipolar cells; RGC: ganglion cells.

These results are illustrated by FIG. 3.

These results show that the RK-Otx2 peptide binds, like AP-Nt-Otx2, to the ganglion and bipolar cells. On the other hand, no binding is observed with the AA-Otx2 peptide. Another peptide (RA-Otx2), in which the RK dipeptide is replaced with RA, binds only very weakly to the ganglion and bipolar cells (results not shown).

In order to verify that the RK-Otx2 peptide indeed had the same binding specificity as AP-Nt-Otx2, the ability of the RK-Otx2 and AA-Otx2 polypeptides to antagonize the binding of AP-Nt-Otx2 was tested. The test for binding of AP-Nt-Otx2 to sections of retinas was carried out as described above, with the exception that the incubation of the supernatant containing AP-Nt-Otx2 was carried out in the presence of 2 µg/ml of the RK-Otx2 peptide or of the AA-Otx2 peptide.

Figure 4:
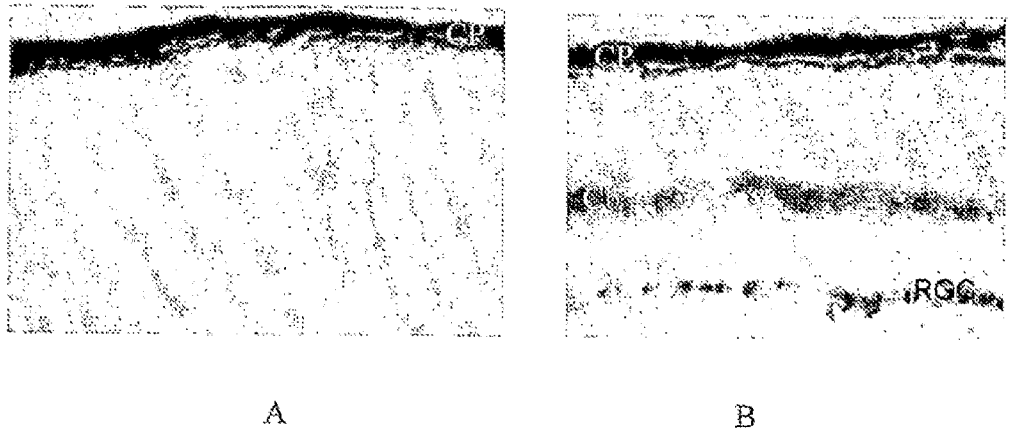
FIG. 4 depicts results obtained with RK-Otx2 and AA-Otx2. A: Binding of AP-Nt-Otx2 in the presence of the RK-Otx2 peptide; B: Binding of AP-Nt-Otx2 in the presence of the AA-Otx2 peptide; CP: Cells of the retinal pigment epithelium; Cb: bipolar cells; RGC: ganglion cells.

The results are illustrated by FIG. 4.

These results show that the RK-Otx2 peptide blocks the binding of AP-Nt-Otx2 to the bipolar cells and to the ganglion cells, whereas the AA-Otx2 peptide has no effect on this binding.

EXAMPLE 2: EFFECT OF A CHIMERIC POLYPEPTIDE ASSOCIATING AN OTX2 FRAGMENT CONTAINING THE CELL TARGETING SEQUENCE WITH A HETEROLOGOUS TRANSCRIPTION-ACTIVATING DOMAIN, ON THE SURVIVAL OF RETINAL GANGLION NEURONS

It has previously been shown (cf. application PCT/FR 2009/000031 of Jan. 9, 2009) that Otx2 protects retinal ganglion neurons against the toxic effects of N-methyl-D-aspartate (NMDA).

A chimeric polypeptide was constructed genetically and produced by bacterial synthesis, by fusing the N-terminal domain of Otx2 and its homeodomain (amino acids 1-97 of Otx2), with the VP16 trans-activator domain of the herpes virus (MLGDGDSPGPGFTPHDSAPYGALDMAD-FEFEQMFTDALGIDEYGG, SEQ ID NO: 4).

C57 B16 mice received, in the right eye, 1 µl of injection buffer (PBS or 9‰ NaCl) containing either 1 mM of NMDA, or 1 mM of NMDA supplemented with 30 ng of the chimeric polypeptide, and in the left eye, the same volume of injection buffer, without additive.

The survival of the ganglion neurons was determined by measuring the level of expression of Brain 3A (Brn3A), a transcription factor which, in the retina, is specifically expressed in the ganglion neurons (Xiang et al., J. Neurosci., 15, 4762-4785, 1995).

After 4 days, the animals are sacrificed, the retinas are removed, and the mRNA is extracted therefrom.

The level of expression of Bm3A mRNA was determined by quantitative RT-PCR using the hypoxanthine phosphoribosyltransferase (HPRT) gene as reference gene, and the ratio between the expression of the Bm3A mRNA in the right eye and in the left eye was calculated.

Figure 5:
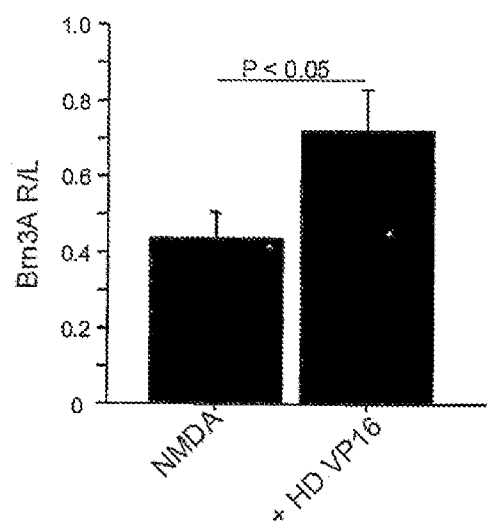
FIG. 5 depicts results for the level of expression of Brn3A mRNA.

The results are illustrated by FIG. 5. The additives used are indicated along the x-axis; the ratio between the amounts of Brn3A mRNA (standardized relative to the HPRT mRNA) in the right eye and in the left eye is indicated along the y-axis.

These results show that NMDA, administered alone, significantly decreases (by approximately 60%) the amount of ganglion neurons, and that the addition of 30 ng of the chimeric polypeptide effectively protects the ganglion neurons against the toxic effects of the NMDA.

EXAMPLE 3: BINDING OF OTX2 TO TARGET CELLS OF THE CEREBRAL CORTEX

The interaction, with the cells of the cerebral cortex, of the AP-Otx2, AP-Nt-Otx2, AP-Hd-Otx2 and AP-HdAA-Otx2 fusion proteins (AP-Nt-Otx2 being a variant of AP-Nt-Otx2 in which the RK amino acid doublet has been replaced with the AA doublet), alone (culture supernatant diluted to $1/20^{th}$) or in the presence of a whole Otx2 (1 µg/ml) or of the RK-Otx2 or AA-Otx2 peptides (2 µg/ml), was tested on cryostat sections of adult mouse brains, using the protocol described in example 1 above.

Figure 6:
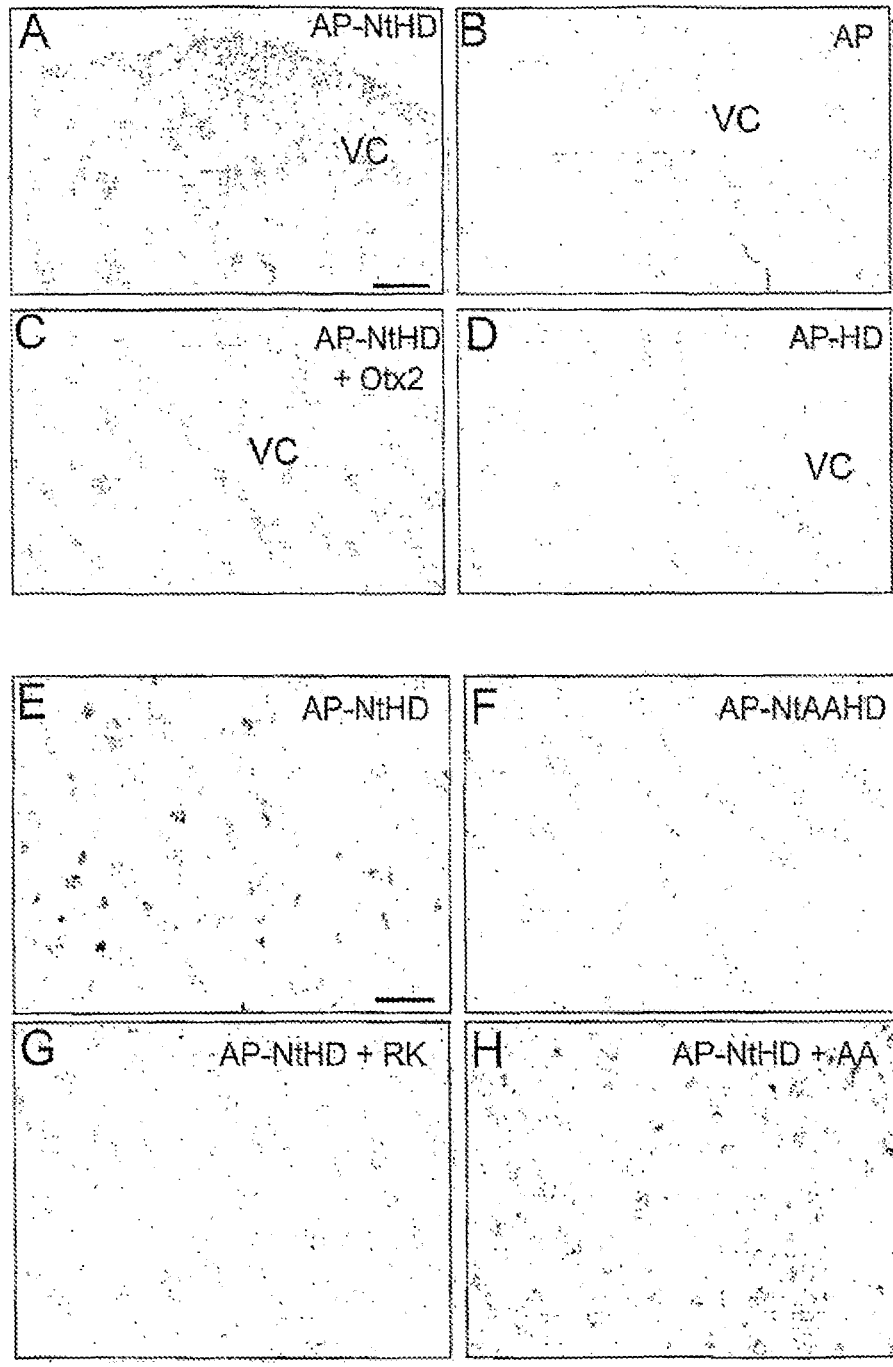
FIG. 6 depicts results obtained with cells of cerebral cortex. A-D, scale bar 500 µm; (A) AP-Nt-Otx2; (B) AP (alkaline phosphatase alone); (C) AP-Nt-Otx2 in the presence of a whole Otx2; (D) AP-Hd-Otx2; E-H, scale bar 100

The results are illustrated by FIG. 6.

These results show that AP-Nt-Otx2 binds to cortical cells, comprising those of the visual cortex; on the other hand, no binding is observed with AP, AP-Hd-Otx2, or AP-HdAA-Otx2. In addition, whole Otx2 and also RK-Otx2, but not AA-Otx2, block the binding of AP-Nt-Otx2 to its target cells.

Glycosaminoglycans (GAGs), and in particular chondroitin sulfate proteoglycans, are an essential constituent of the extracellular matrix (perineuronal net) which surrounds the parvalbumin neurons of the visual cortex. The putting into place of this perineuronal net coincides with the end of the critical period of plasticity; it constitutes a major factor in the loss of cortical plasticity that occurs at the end of this critical period, and it has been shown that the destruction of this perineuronal net by treating with chondroitinase-ABC makes it possible to restore this plasticity (Pizzorusso et al., Science, 298, 1248-51, 2002).

In order to determine whether the perineuronal net associated with parvalbumin neurons was involved in the binding between AP-Nt-Otx2 and its target cells, the binding of AP-Otx2 was tested on cryostat sections of adult mouse brains fixed with methanol, and then incubated for 24 hours in the presence of chondroitinase ABC (2 U/ml) in a buffer containing 50 mM Tris [pH 8.0], 40 mM of sodium acetate, 0.1% BSA and protease inhibitors. In parallel, the sections, untreated or treated with chondroitinase ABC, were incubated with 0.01 mg/ml of *Wisteria floribunda agglutinin* lectin (WFA; Sigma-Aldrich), which binds to the GAGs of the perineuronal net, and which is labeled with FITC.

The results are illustrated by FIG. 7.

These results show that the treatment with chondroitinase ABC, which destroys the GAGs of the perineuronal net, also abolishes the binding of AP-Nt-Otx2.

It therefore appears that it is the GAGs of the perineuronal net associated with the parvalbumin neurons which bear the AP-Nt-Otx2 binding site.

EXAMPLE 4: IN VIVO BLOCKING OF THE ENDOGENOUS TRANSFER OF OTX2 BY THE RK-OTX2 PEPTIDE

As shown above, the RK-Otx2 peptide can block the binding of Otx2 to its target cells, in vitro. It was tested whether this effect also occurred in vivo.

For this purpose, the RK-Otx2 peptide (0.25 mg/ml), the AA-Otx2 peptide (0.25 mg/ml), or PBS buffer, combined with polysialic acid (0.25 mg/ml, in order to enable diffusion of the peptides and to avoid nonspecific binding thereof to neurons expressing polysialic acid at their surface), were slowly infused (1 µl/h) for 7 days into the right visual cortex of adult mice, using osmotic minipumps (Alzet 1003D, Alza) connected to stereotaxically implanted cannulas (Hensch et al., Science, 282, 1504-8, 1998; Fagiolini & Hensch, Nature, 404, 183-6, 2000). At the end of the infusion, the mice are perfused with 4% PFA, and brain sections (25 µm) are cut in order to study the localization of Otx2 and that of the RK-Otx2 peptide. Otx2 is visualized using a rat anti-Otx2 monoclonal antibody diluted to $1/200$ (Sugiyama et al., Cell, 134, 508-20, 2008), followed by a donkey anti-rat antibody labeled with Alexa 488 (Molecular Probes), diluted to $1/2000$. The RK-Otx2 peptide is visualized using streptavidin labeled with Cy5.

The cells expressing Otx2 were counted over a surface area of 700×350 μm encompassing layers I/II and IV of the binocular zone of the visual cortex.

The results are illustrated by FIG. 8.

These results show that the infusion of the RK-Otx2 peptide into the visual cortex for 7 days significantly reduces the number of cells expressing Otx2. On the other hand, in the case of the AA-Otx2 peptide, only a small, insignificant reduction is observed in the number of cells expressing Otx2.

It was verified, by Sytox green labeling, that the infusion had no effect in itself on the number of cells. In order to be sure that the decrease in the number of cells expressing Otx2 was not due to cell death, an infusion of this peptide was carried out according to the protocol described above, and the number of cells expressing Otx2 was measured 8 days after the end of the infusion. Under these conditions, only very small amounts of RK-Otx2 peptide are detected 8 days after the end of infusion, and the number of cells expressing Otx2 in the treated hemisphere is restored to the level of that of the control hemisphere.

EXAMPLE 5: RESTORATION OF CORTICAL PLASTICITY BY THE RK-OTX2 PEPTIDE

The effects of the RK-Otx2 peptide on the plasticity of the ocular cortex were compared with those of chondroitinase-ABC, which is known to enable the restoration of this plasticity (Pizzorusso et al., Science, 298, 1248-51, 2002).

The RK-Otx2 peptide or the AA-Otx2 peptide was infused in adult mice (therefore after closing of the critical period of plasticity), as described in example 4 above. Chondroitinase-ABC, or the injection buffer (deionized water+0.1% BSA), were injected (0.4 μl for each injection) at 3 sites surrounding the visual cortex (AP lambda, LM 1.5 mm; AP lambda, 4.0 mm; AP+1.5 mm; LM 2.5 mm) at two different depths (300 and 500 μm).

After infusion of the peptides or injection of chondroitinase ABC, the mice are subjected to monocular deprivation for 4 days, and the responses to visual stimuli are then measured by single-unit extracellular electrophysiology. The electrophysiology recordings are carried out under nembutal/chlorprothixene anesthesia using standard techniques (Gordon & Stryker, J Neurosci, 16, 3274-86, 1996; Mataga et al., Neuron, 44, 1031-41, 2004). 5 to 7 single-unit recordings were carried out for each mouse, on both sides of the medial-lateral axis of the primary visual cortex, in order to cover the monocular zone and the binocular zone, and to avoid sampling biases. Cell dominance scores were assigned to the cell responses, using a 7-point classification system (Wiesel & Hubel, J Neurophysiol, 26, 978-93, 1963) (Gordon & Stryker, J Neurosci, 16, 3274-86, 1996). The ocular dominance in the binocular zone was calculated for each mouse according to a contralateral bias index (CBI), determined as follows:

(CBI): $[(n_1-n_7)+\frac{2}{3}(n_2-n_6)+\frac{1}{3}(n_3-n_5)+N]/2N$, where N=total number of cells and nx=number of cells corresponding to an ocular dominance score of x.

This weighted mean of the bias in favor of one or other eye can range from 0, for complete ipsilateral dominance, to 1, for complete contralateral dominance.

In addition, treated mouse brain frontal sections were prepared, as described in example 4 above, in order to determine the influence of the RK-Otx2 peptide on parvalbumin neurons. The sections were labeled either with WFA, as described in example 3, or using a mouse anti-parvalbumin monoclonal antibody (1/500, Sigma-Aldrich), which was visualized using a donkey anti-mouse antibody labeled with Cy3. The labeled cells were quantified as described in example 4.

The results are illustrated by FIG. 9.

These results show that the monocular deprivation induces an ocular dominance (decrease in the contralateral bias index from 0.7 to 0.57) in the adult mice treated with the RK-Otx2 peptide, as in those treated with the chondroitinase ABC (chABC), unlike the mice treated with the injection buffer or the AA-Otx2 peptide.

In parallel, the infusion of the RK-Otx2 peptide (but not that of the AA-Otx2 peptide) decreases the expression of the sites for the binding of WFA, and also that for parvalbumin. The number of parvalbumin-positive cells decreases by 56.2%, and that of cells surrounded by sites for the binding of WFA decreases by 51.3%.

It emerges from these results that the blocking of Otx2 transfer by the RK-Otx2 peptide causes the inhibition of parvalbumin expression, and also a destruction of the perineuronal net similar to that caused by chondroitinase ABC. This results in a return of the parvalbumin neurons to an immature state, similar to that normally observed during the critical period, and this immature state enables reopening of the critical period, and restoring of the plasticity that is associated therewith.

The invention claimed is:

1. A method of delivering a polypeptide molecule to an Orthodenticle Homeobox 2 (Otx2) target cell selected from retinal ganglion neurons, retinal bipolar neurons and parvalbumin neurons, comprising
contacting the target cell with a chimeric polypeptide consisting of:
(i) a targeting peptide consisting of the amino acid sequence SEQ ID NO: 2 bonded with
(ii) a heterologous polypeptide molecule which is not an Otx2 protein, wherein the targeting peptide is located at the C-terminus of the chimeric polypeptide.

2. A method of delivering a polypeptide molecule to an Otx2 target cell selected from retinal ganglion neurons, retinal bipolar neurons and parvalbumin neurons in a subject comprising delivering a polypeptide molecule to the target cell according to the method of claim 1, wherein the delivering comprises administering the polypeptide molecule to the subject by infusion.

3. A method of delivering a polypeptide molecule to an Orthodenticle Homeobox 2 (Otx2) target cell selected from retinal ganglion neurons, retinal bipolar neurons and parvalbumin neurons, comprising
contacting the target cell with a chimeric polypeptide consisting of:
(i) a targeting peptide consisting of the amino acid sequence of SEQ ID NO: 2 bonded with
(ii) a heterologous polypeptide molecule which is not an Otx2 protein, and
(iii) a VP16 trans-activator domain of herpes virus,
wherein the targeting peptide is located at the C-terminus of the chimeric polypeptide.

4. The method according to claim 3, wherein the VP16 trans-activator domain contains the amino acid sequence of SEQ ID NO: 4.

5. A method of delivering a polypeptide molecule to an Otx2 target cell selected from retinal ganglion neurons, retinal bipolar neurons and parvalbumin neurons in a subject comprising delivering a polypeptide molecule to the target cell according to the method of claim 3, wherein the delivering comprises administering the polypeptide molecule to the subject by infusion.

\* \* \* \* \*